US007232788B2

(12) United States Patent
Liang et al.

(10) Patent No.: US 7,232,788 B2
(45) Date of Patent: Jun. 19, 2007

(54) MIXED METAL OXIDE CATALYSTS FOR THE PRODUCTION OF UNSATURATED ALDEHYDES FROM OLEFINS

(75) Inventors: Wugeng Liang, Katy, TX (US); Scott A. Stevenson, Houston, TX (US); James W. Kauffman, Katy, TX (US); John S. Ledford, Mason, OH (US); Joseph R. Linzer, Houston, TX (US)

(73) Assignee: Saudi Basic Industries Corporation, Riyadh (SA)

( * ) Notice: Subject to any disclaimer, the term of this patent is extended or adjusted under 35 U.S.C. 154(b) by 43 days.

(21) Appl. No.: 11/079,038

(22) Filed: Mar. 14, 2005

(65) Prior Publication Data

US 2005/0159621 A1 Jul. 21, 2005

Related U.S. Application Data

(63) Continuation-in-part of application No. 10/403,213, filed on Mar. 31, 2003, now abandoned.

(51) Int. Cl.
*B01J 23/00* (2006.01)
*B01J 21/00* (2006.01)
*B01J 20/00* (2006.01)

(52) U.S. Cl. ...................... 502/311; 502/240; 502/255; 502/263; 502/305; 502/313; 502/314; 502/315; 502/316; 502/321; 502/322; 502/349; 502/350; 502/415; 502/439

(58) Field of Classification Search ................ 502/255, 502/305, 311–313, 316, 321, 322, 350, 349, 502/240, 263, 439, 415
See application file for complete search history.

(56) References Cited

U.S. PATENT DOCUMENTS 4,083,805 A * 4/1978 White et al. ................ 502/179
4,111,985 A * 9/1978 Okada et al. ............... 562/546
4,155,938 A * 5/1979 Yamamoto et al. ......... 568/479
4,162,234 A * 7/1979 Grasselli et al. ............ 502/205
4,192,776 A * 3/1980 Grasselli et al. ............ 502/205
4,250,339 A * 2/1981 Sakamoto et al. .......... 568/471
4,272,637 A * 6/1981 Yamamoto et al. ......... 568/780
4,280,928 A * 7/1981 Kirch et al. ................ 502/205
4,301,030 A * 11/1981 Shaw et al. ................. 502/209
4,359,407 A * 11/1982 Dolhyj et al. .............. 502/209
4,438,217 A * 3/1984 Takata et al. ............... 502/205
4,511,671 A * 4/1985 Saito et al. ................. 502/242
4,537,874 A * 8/1985 Sato et al. .................. 502/311
4,556,731 A * 12/1985 Guttmann et al. .......... 562/546
4,560,673 A * 12/1985 Shaw ........................ 502/206
4,816,603 A * 3/1989 Oh-Kita et al. ............. 562/538
4,843,055 A * 6/1989 Glaeser et al. .............. 502/202
4,873,217 A * 10/1989 Kawajiri et al. ........... 502/311
5,093,299 A * 3/1992 Suresh et al. ............... 502/212
5,138,100 A * 8/1992 Matsuura .................... 568/474
5,208,371 A * 5/1993 Kuroda et al. .............. 562/538
5,212,137 A * 5/1993 Suresh et al. ............... 502/212
5,225,389 A * 7/1993 Caillod et al. ............. 502/205
5,245,083 A * 9/1993 Matsuura .................... 568/479
5,276,178 A * 1/1994 Onodera et al. ............ 562/537
5,532,199 A * 7/1996 Watanabe et al. ........... 502/311
5,663,113 A * 9/1997 Midorikawa et al. ....... 502/314
5,700,752 A * 12/1997 Kurimoto et al. ........... 502/311
5,728,894 A * 3/1998 Nagano et al. ............. 568/479
5,856,259 A * 1/1999 Watanabe et al. ........... 502/305
5,892,108 A * 4/1999 Shiotani et al. ............. 562/532
5,910,608 A * 6/1999 Tenten et al. ............... 562/532
6,169,214 B1 * 1/2001 Tenten et al. ............... 568/476
6,383,973 B1 * 5/2002 Kimura et al. .............. 502/300
6,420,307 B1 * 7/2002 Wu et al. ................... 502/300
6,583,316 B1 * 6/2003 Onodera et al. ............ 562/537

* cited by examiner

*Primary Examiner*—Cam N. Nguyen
(74) *Attorney, Agent, or Firm*—Jim Wheelington

(57) ABSTRACT

A catalyst for production of unsaturated aldehydes, such as methacrolein, by gas phase catalytic oxidation of olefins, such as isobutylene, contains oxides of molybdenum, bismuth, iron, cesium and, optionally, other metals. The catalyst has a certain relative amount ratio of cesium to bismuth, a certain relative amount ratio of iron to bismuth and a certain relative amount ratio of bismuth, iron, cesium and certain other metals to molybdenum and, optionally, tungsten. For a catalyst of the formula:

$$Mo_{12}Bi_aW_bFe_cCo_dNi_eSb_fCs_gMg_hZn_iP_jO_x$$

wherein a is 0.1 to 1.5, b is 0 to 4, c is 0.2 to 5.0, d is 0 to 9, e is 0 to 9, f is 0 to 2.0, g is from 0.4 to 1.5, h is 0 to 1.5, i is 0 to 2.0, j is 0 to 0.5 and x is determined by the valences of the other components, c:g=3.3–5.0, c:a=2.0–6.0 and (3a+3c+2d+2e+g+2h+2i)/(2×12+2b)=0.95–1.10.

11 Claims, No Drawings

MIXED METAL OXIDE CATALYSTS FOR THE PRODUCTION OF UNSATURATED ALDEHYDES FROM OLEFINS

This is a continuation-in-part application of application Ser. No. 10/403,213 filed Mar. 31, 2003, now abandoned.

BACKGROUND OF THE INVENTION

1. Field of the Invention

This invention relates to a mixed metal oxide catalyst containing oxides of molybdenum, bismuth, iron, cesium and, optionally, other metals for the production of unsaturated aldehydes from olefins, such as methacrolein by gas phase catalytic oxidation of isobutylene in the presence of air or another gas containing molecular oxygen.

2. Description of the Prior Art

Many catalysts have been disclosed for use in the production of acrolein or methacrolein by catalytic vapor phase oxidation of propylene or isobutylene. U.S. Pat. No. 4,816,603 discloses a catalyst for production of methacrolein and methacrylic acid of the formula:

$$Mo_aW_bBi_cFe_dNi_eSb_fX_gY_hZ_iA_jO_k$$

where X is potassium, rubidium and/or cesium, Y is phosphorus, sulfur, silicon, selenium, germanium and/or boron, Z is zinc and/or lead, A is magnesium, cobalt, manganese and/or tin, a is 12, b is 0.001 to 2, c is 0.01 to 3, d is 0.01 to 8, e is 0.01 to 10, f is 0.01 to 5, g is 0.01 to 2, h is 0 to 5, i is 0.01 to 5, j is 0 to 10 and k is sufficient to satisfy the valences.

U.S. Pat. No. 4,511,671 discloses a catalyst for manufacturing methacrolein of the formula:

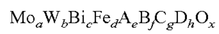

$$Mo_aW_bBi_cFe_dA_eB_fC_gD_hO_x$$

where A is at least one of nickel and/or cobalt; B is at least one of alkali metals, alkaline earth metals and/or thallium; C is at least one of phosphorus, tellurium, antimony, tin, cerium, lead, niobium, manganese and/or zinc; D is at least one of silicon, aluminum, zirconium, and/or titanium; a is 12, b is 0 to 10, c is 0.1 to 10, d is 0.1 to 20, e is 2 to 20, f is 0 to 10, g is 0 to 4, h is 0 to 30 and x is determined by the atomic valences.

U.S. Pat. No. 4,556,731 discloses a catalyst for production of methacrolein and methacrylic acid of the formula:

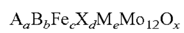

$$A_aB_bFe_cX_dM_eMo_{12}O_x$$

where A is an alkali metal, such as potassium, rubidium, cesium or mixtures thereof, thallium, silver or mixtures thereof, B is cobalt, nickel, zinc, cadmium, beryllium, calcium, strontium, barium, radium or mixtures thereof, X is bismuth, tellurium or mixtures thereof and M is (1) Cr+W, Ge+W, Mn+Sb, Cr+P, Ge+P, Cu+W, Cu+Sn, Mn+Cr, Pr+W, Ce+W, Sn+Mn, Mn+Ge or combinations thereof, (2) Cr, Sb, Ce, Pn, Ge, B, Sn, Cu or combinations thereof, or (3) Mg+P, Mg+Cu, Mg+Cr, Mg+Cr+W, Mg+W, Mg+Sn or combinations thereof, a is 0 to 5, b is 0 to 20, c is 0 to 20, d is 0 to 20, e is 0.01 to 12 and x satisfies the valence requirements.

U.S. Pat. No. 5,245,083 discloses a catalyst for preparing methacrolein of a mixture of composition (1) of the formula:

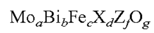

$$Mo_aBi_bFe_cX_dZ_fO_g$$

where X is Ni and/or Co, Z is at least one of W, Be, Mg, S, Ca, Sr, Ba, Te, Se, Ce, Ge, Mn, Zn, Cr, Ag, Sb, Pb, As, B, P, Nb, Cu, Cd, Sn, Al, Zr and Ti, a is 12 b is 0.1 to 10, c is 0 to 20, d is 0 to 20, f is 0 to 4 and g satisfies the valence requirement and composition (2) of the formula:

$$A_mMo_nO_p$$

where A is at least one of K, Rb and Cs, m is 2, n is 1 to 9 and p is 3n+1.

U.S. Pat. No. 5,138,100 discloses a catalyst for preparing methacrolein with a mixture of composition (1) of the formula:

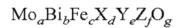

$$Mo_aBi_bFe_cX_dY_eZ_fO_g$$

where X is at least one of Ni and Co, Y is at least one of K, Rb, Cs and Ti, Z is at least one of the elements belonging to Groups 2, 3, 4, 5, 6, 7, 11, 12, 13, 14, 15 and 16, specifically beryllium, magnesium, calcium, strontium, barium, titanium, zirconium, cerium, niobium, chromium, tungsten, manganese, copper, silver, zinc, cadmium, boron, aluminum, germanium, tin, lead, phosphorus, arsenic, antimony, sulfur, selenium and tellurium, a is 12, b is 0.1 to 10, c is 0 to 20, d is 0 to 20, e is 0 to 2, f is 0 to 4, and g satisfies the valence requirement and composition (2) of the formula:

$$Ln_hMo_iO_j$$

where Ln is at least one of the rare earth elements, h is 0.2 to 1.5, i is 1 and j satisfies the valence requirement. The atomic ratio of the rare earth element to molybdenum is disclosed to be in the range from 0.2 to 1.5 with an atomic ratio less than 0.2 resulting in high selectivity but poor activity and with an atomic ratio greater than 1.5 resulting in high activity but poor selectivity.

U.S. Pat. No. 4,537,874 discloses a catalyst for production of unsaturated aldehydes of the formula:

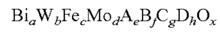

$$Bi_aW_bFe_cMo_dA_eB_fC_gD_hO_x$$

where A is nickel and/or cobalt, B is at least one of alkali metal, alkaline earth metals and thallium, C is at least one of phosphorus, arsenic, boron, antimony, tin, cerium, lead and niobium, D is at least one of silicon, aluminum, zirconium and titanium, a is 0.1 to 10.0, b is 0.5 to 10.0, c is 0.1 to 10.0, d is 12, e is 2.0 to 20.0, f is 0.001 to 10.0, g is 0 to 10.0 and h satisfies the valence requirement. The ratio of a/b is 0.01 to 6.0 so that bismuth is combined very stably with tungsten and compounds such as bismuth trioxide and bismuth molybdate are not formed.

U.S. Pat. No. 5,728,894 discloses a catalyst for producing methacrolein of the formula:

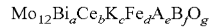

$$Mo_{12}Bi_aCe_bK_cFe_dA_eB_fO_g$$

where A is Co or a mixture of Co and Mg having an atomic ratio of Mg to Co not more than 0.7, B is Rb, Cs or a mixture thereof, a is 0 to 8, b is 0 to 8, c is 0 to 1.2, d is 0 to 2.5, e is 1.0 to 12, f is 0 to 2.0, g satisfies the valence requirement. The relative atomic ratio of iron to bismuth and cerium should be $0<d/(a+b+d)\leqq 0.9$. The relative atomic ratio of bismuth, cerium and potassium should be $0.05\leqq b/(a+b+c)\leqq 0.7$. The relative atomic ratio of potassium to bismuth and cerium should be $0<c/(a+b+c)\leqq 0.4$. Bismuth, cerium, potassium, iron and cobalt are indispensable elements for the disclosed invention.

U.S. Pat. No. 5,166,119 discloses a method for preparing a catalyst of molybdenum, bismuth, iron and cesium or thallium for producing methacrolein and methacrylic acid by gas phase catalytic oxidation of isobutylene or tert-butanol with molecular oxygen. There is no preference disclosed of cesium over thallium.

Prior art discloses mixed metal oxide catalysts which contain molybdenum, bismuth, iron, cesium and other metals for the production of methacrolein. Furthermore, prior art discloses certain ranges of amounts of these metals. Some prior art discloses relative ratios of certain components to other components. The effect of the selection of certain components for a mixed metal oxide catalyst for the production of methacrolein and the relative relationship of some of these components to other components has not been investigated in complete detail.

SUMMARY OF THE INVENTION

The present invention is for a catalyst of the general formula:

$$Mo_{12}Bi_aW_bFe_cCs_gM_mO_x$$

wherein a is in the range from 0.1 to 1.5, b is in the range from 0 to 9, c is in the range from 0.2 to 5.0, g is in the range from 0.1 to 1.5, M is one or more selected from calcium, strontium, lithium, sodium, selenium, cobalt, nickel, magnesium, zinc, potassium, rubidium, thallium, manganese, barium, chromium, tin, lead, cadmium and copper, m is in the range from 0 to 9, x is determined by the valences of the other components. Other components, such as cerium, antimony, phosphorus, boron, sulfur, silicon, aluminum, titanium, tellurium, vanadium, zirconium and niobium may also be present. The catalyst of the present invention has a relative amount ratio of iron to cesium which is in the range of 3.3 to 5.0, i.e., c:g=3.3–5.0, a relative amount ratio of iron to bismuth which is in the range of 2.0 to 6.0, i.e., c:a=2.0–6.0 and a relative amount of bismuth, iron and cesium to molybdenum and tungsten which is in the range of 0.95 to 1.10, i.e., $(3a+3c+g+\Sigma v_n m_n)/(2\times 12+2b)=0.95$ to 1.10 with v being the valence of each M, m being the relative amount of each M and n being the total number of M metal(s) present in the catalyst. The process of making the catalyst is generally to dissolve the metal compounds of molybdenum, bismuth, iron, cesium and, optionally, other metals, such as tungsten, calcium, strontium, lithium, sodium, selenium, cobalt, nickel, magnesium, zinc, potassium, rubidium, thallium, manganese, barium, chromium, tin, lead, cadmium, copper, cerium, antimony, phosphorus, boron, sulfur, silicon, aluminum, titanium, tellurium, vanadium, zirconium and niobium, and precipitate a catalyst precursor which is calcined to form a mixed metal oxide catalyst. The metal compounds may be salts (e.g., nitrates, halides, ammonium, organic acid, inorganic acid), oxides, hydroxides, carbonates, oxyhalides, sulfates and other groups which may exchange with oxygen under high temperatures so that the metal compounds become metal oxides. In one embodiment of the invention, the metal compounds are soluble in water or an acid. In another embodiment of the invention the molybdenum compound and the tungsten compound are ammonium salts, the phosphorus compound is phosphoric acid, and that the bismuth compound, the ferric compound, the nickel compound, the cobalt compound, the magnesium compound, the zinc compound, the cesium compound, the potassium compound, the rubidium compound, the thallium compound, the manganese compound, the barium compound, the chromium compound, the boron compound, the sulfur compound, the silicon compound, the aluminum compound, the titanium compound, the cerium compound, the tellurium compound, the tin compound, the vanadium compound, the zirconium compound, the lead compound, the cadmium compound, the copper compound and the niobium compound are nitrates, oxides or acids and the antimony compound is an oxide.

The process of using the catalyst is generally in a gas phase catalytic oxidation of an olefin to an aldehyde by contacting an olefin, such as propylene or isobutylene, and a molecular oxygen-containing gas in the presence of the catalyst of the present invention to form an aldehyde. The use of the catalyst of the present invention in this process increases activity and selectivity to the production of methacrolein.

DESCRIPTION OF EMBODIMENTS OF THE INVENTION

According to the present invention, a catalyst is provided for producing acrolein or methacrolein by oxidation of propylene or isobutylene. The oxidation is a catalytic reaction that converts an olefin in the presence of oxygen to an unsaturated aldehyde and water:

$$H_2C{=}CA\text{-}CH_3+O_2\text{->}H_2C{=}CA\text{-}CHO+H_2O$$

where A is hydrogen or an alkyl group. Carboxylic acid is also produced in a side reaction.

The catalyst is a mixed metal oxide of the formula:

$$Mo_{12}Bi_aW_bFe_cCs_gM_mO_x$$

wherein a is in the range from 0.1 to 1.5, b is 0 to 9, c is in the range from 0.2 to 5.0, g is in the range from 0.1 to 1.5, with a relative amount ratio of iron to cesium in the range of 3.3 to 5.0, i.e., c:g=3.3–5.0, and a relative amount ratio of iron to bismuth in the range of 2.0 to 6.0, i.e., c:a=2.0–6.0, M is one or more selected from calcium, strontium, lithium, sodium, selenium, cobalt, nickel, magnesium, zinc, potassium, rubidium, thallium, manganese, barium, chromium, tin, lead, cadmium and copper, m is in the range from 0 to 9 and x is determined by the valences of the other components, with the relative amount ratio of bismuth, iron, cesium, and any and all M metals to molybdenum and tungsten represented by the formula $(3a+3c+g+\Sigma v_n m_n)/(2\times 12+2b)=0.95–1.10$ wherein $\Sigma v_n m_n$ is the sum of the product of the valance (v) and the relative amount of each M (m), n being the total number of M metal(s) present in the catalyst. For example, if M were nickel (v=2, n=1) and cobalt (v=2, n=2) present in the amounts of 4.0 and 0.5, respectively, $\Sigma v_n m_n$ would be (2×4.0)+(2×0.5)=9. In an embodiment of the invention for a catalyst for producing methacrolein by oxidation of isobutylene, g is in the range from 0.4 to 1.5.

U.S. Pat. No. 5,728,894 discloses three relationships of relative atomic ratios:

iron to bismuth and cerium: $0<d/(a+b+d)\leqq 0.9$ bismuth, cerium and potassium: $0.05\leqq b/(a+b+c)\leqq 0.7$ potassium to bismuth and cerium: $0<c/(a+b+c)\leqq 0.4$ The first relationship of relative atomic ratios defines the relative amount of iron to bismuth. Based on this relationship, the iron content should be less than the bismuth content, which can be seen in the examples of U.S. Pat. No. 5,728,894. The relationship disclosed in the present invention is to the contrary in that the iron content is greater than the bismuth content, i.e., c:a=2.0–6.0.

The second relationship of relative atomic ratios defines the relative amount of cerium content. Cerium is not a required element of the catalyst of the present invention. U.S. Pat. No. 5,728,894 discloses cerium as an indispensable element of this prior art catalyst.

The third relationship of relative atomic ratios defines the relative amount of alkaline metals in the catalyst to the bismuth content. In the catalyst of the present invention, the relative amount of alkaline metals to bismuth is greater than the upper limit disclosed in U.S. Pat. No. 5,728,894 (0.4).

In the catalyst of U.S. Pat. No. 5,728,894, cerium, potassium and cobalt are indispensable elements while in the catalyst of the present invention these elements are optional.

In an embodiment of the present invention, the catalyst is of the formula:

$$Mo_{12}Bi_aW_bFe_cCs_gM_mM'_{m'}O_x$$

wherein M' is one or more of cerium, antimony, phosphorus, boron, sulfur, silicon, aluminum, titanium, tellurium, vanadium, zirconium and niobium and m' is from 0 to 9. M' and m' would not be taken into account in the formulae above for relative amounts of components.

In another embodiment of the invention the catalyst is of the formula:

$$Mo_{12}Bi_aW_bFe_cCo_dNi_eSb_fCs_gMg_hZn_iP_jO_x$$

wherein b is 0 to 4, d is 0 to 9, e is 0 to 9, f is 0 to 2.0, h is 0 to 1.5, c:g is in the range of 3.3–4.8, c:a is in the range of 2.4–4.8, and the relative amount of bismuth, iron, cesium, cobalt, nickel, magnesium, and/or zinc to molybdenum and tungsten is represented by the formula $(3a+3c+2d+2e+2h+2i)/(2\times12+2b)=0.95–1.09$.

The process of making the catalyst is generally to dissolve the metal compounds in water or in an acid, precipitate a solid catalyst precursor to form a slurry, separate the solid by removing liquid from the slurry to leave a solid, dry the solid, and calcine the solid to form a mixed metal oxide catalyst. The metal compounds may be salts (e.g., nitrates, halides, ammonium, organic acid, inorganic acid), oxides, hydroxides, carbonates, oxyhalides, sulfates and other groups which may exchange with oxygen under high temperatures so that the metal compounds become metal oxides. In one embodiment of the invention, the metal compounds are soluble in water or an acid. In another embodiment of the invention the molybdenum compound and the tungsten compound are ammonium salts, such as ammonium paramolybdate or ammonium molybdate and ammonium paratungstate or ammonium tungstate, respectively, the phosphorus compound is phosphoric acid, the bismuth, iron, cobalt, nickel, cesium, magnesium, zinc, phosphorus, potassium, rubidium, thallium, manganese, barium, chromium, boron, sulfur, silicon, aluminum, titanium, cerium, tellurium, tin, vanadium, zirconium, lead, cadmium, copper and niobium compounds are nitrates, oxides or acids, the antimony compound is an oxide, such as antimony oxide or antimony trioxide, the calcium, strontium, lithium and sodium compounds are nitrates or carbonates and the selenium compound is an oxide. In one embodiment of the invention, the bismuth, iron, cesium, cobalt, nickel, magnesium and zinc compounds are nitrates.

The present invention does not depend on a particular order of addition of the components. While a particular order of addition of the various metal compound components may affect the performance of the catalyst, the present invention is directed toward the particular relative amount of certain components to other components without regard to the order in which the steps in the process of making the catalyst occur.

An example of making the catalyst of the claimed invention is to dissolve an ammonium salt of molybdenum, such as ammonium paramolybdate or ammonium molybdate and, optionally, an ammonium salt of tungsten, such as ammonium paratungstate or ammonium tungstate, and phosphoric acid in water, dissolve a bismuth nitrate in an acid, dissolve an iron nitrate and, optionally, a cobalt nitrate, a nickel nitrate, a magnesium nitrate, and a zinc nitrate in water or in the acid with the bismuth nitrate, mix the solutions at a temperature in the range from 40° C. to 100° C., or at 60° C. to 95° C., to obtain a precipitate to form a slurry and then add a cesium nitrate and, optionally, an antimony oxide to the slurry while maintaining the temperature. The cesium nitrate and the antimony oxide may be added to the slurry as solids. The slurry may be aged for 2 to 24 hours, for 8 to 18 hours or for 5 to 10 hours. The liquid of the slurry is removed by evaporation and the solid precipitate is dried and calcined to obtain a catalyst. The liquid may be removed and the solid precipitate dried at the same time by spray drying. The liquid may be evaporated at a temperature of 50° to 125° C.

Drying of the catalyst precursor may be in air or an inert gas and in an oven or a spray dryer. In one embodiment of the invention, drying is in an oven in air at a temperature of 100–150° C. for 2–5 hours.

One purpose of calcination of the catalyst precursor is to obtain an oxide of the metal components. The catalyst precursor may be calcined at a temperature of 200–600° C. for 1–12 hours. Calcination may be in two stages, one at a temperature of 150–400° C. for 1–5 hours and another at a temperature of 400–600° C. for 4–8 hours with a temperature ramp of 1–20° C./min, or of 5–10° C./min. In an embodiment of the invention for a two-stage calcination, the first is at a temperature of 290–310° C. for 2 hours and second at a temperature of 460–500° C. for 6 hours. Denitrification may occur in the first step. In the alternative, calcination is in one stage by increasing the temperature from ambient temperature to about 485° C. over two hours instead of an initial step or denitrification. Calcination may be done in a high temperature oven or kiln.

The catalyst may be processed by sieving, forming and other means known in the art to obtain catalyst particles of a certain size. Desired particle size and particle size distribution are related to the design of the reactor (size, shape, configuration, etc.), to the pressure drop intended for the process and to the process flow. For a two stage calcination, the catalyst may be sieved or formed after the first stage calcination and before the second stage calcination. In a commercial process the catalyst precursor may be sieved and formed after spray drying and before calcination.

The X-ray diffraction pattern of the mixed metal oxide compounds is descriptive of the catalyst made by the process of the present invention. The catalyst compositions of the Examples above have a characteristic X-ray diffraction having diffraction peaks at the diffraction angles of 2θ, measured by using Cu Kα radiation, at 25.5, 26.6 and 28.0 (+/−0.1°). There may be several additional diffraction peaks present in a catalyst composition of the present invention but these peaks will normally be evident.

The catalyst of the present invention may be used as an unsupported catalyst or a supported catalyst. The surface area of an unsupported catalyst is from 0.1 to 150 $m^2/g$ or from 1 to 20 $m^2/g$. If supported, the support should be an inert solid which is chemically unreactive with any of the active components of the catalyst and in one embodiment of the invention is silica, alumina, niobia, titania, zirconia or mixtures thereof. The catalyst may be affixed to the support by methods known in the art, including incipient wetness, slurried reactions and spray drying. The catalyst, supported or unsupported, is not limited by shape, size or particle distribution and may be formed as appropriate for the reaction vessel in the process. Examples are powder, granules, spheres, cylinders, saddles, etc.

The catalyst is used in the gas phase catalytic oxidation of a feedstock gas comprising an olefin, such as propylene or isobutylene, with a molecular oxygen-containing gas, such as oxygen, to produce an aldehyde, such as acrolein or methacrolein. Oxygen may be supplied in the pure form or in an oxygen-containing gas, such as air or as an oxygen-diluent gas mixture. The diluent gas may be nitrogen, a hydrocarbon which is gaseous under the process conditions or carbon dioxide. Water and/or an inert gas, such as nitrogen, may also be present. In one embodiment of the invention, the reaction temperature is from 250–450° C. or from 330–410° C. The reactor may be a fixed bed or a fluidized bed reactor. Reaction pressure may be from 0 to 100 psig or from 0 to 55 psig. Space velocity may be from 1000 to 12,500 $hr^{-1}$, 5000 to 10,000 $hr^{-1}$ or 7500 to 10,000 $hr^{-1}$. Operating conditions will depend upon the specifics of catalyst performance and the economics of process design for the individual process.

The invention having been generally described, the following examples are given as particular embodiments of the invention and to demonstrate the practice and advantages thereof. It is understood that the examples are given by way of illustration and are not intended to limit the specification or the claims to follow in any manner.

EXAMPLE 1

43.57 g of ammonium paramolybdate and 1.65 g of ammonium paratungstate were added into 87 ml of de-ionized water. The mixture was stirred and heated to 95° C. to form a solution.

A second solution was prepared by adding 1.3 ml of 70% nitric acid to 9.3 ml of de-ionized water. 9.98 g of bismuth nitrate was dissolved in the nitric acid solution. To this solution was added 19.94 g of ferric nitrate, 23.92 g nickel nitrate, 12.03 g of cobalt nitrate, 2.64 g of magnesium nitrate, 3.24 g of zinc nitrate and 85.3 ml of de-ionized water.

The second solution was added to the first solution dropwise. Precipitates were formed during the addition which created a slurry.

2.41 g of cesium nitrate and 2.11 g of antimony oxide were added as solids to the slurry.

The slurry was aged for 10 hours at 80° C. while being stirred. After aging, the liquid was evaporated at 100° C. The solid was dried at 120° C. for 3 hours. The dried solid was calcined at 300° C. for 2 hours in flowing air. The calcined solid was sieved to a mesh size of 20–30. The sieved solid was calcined at 500° C. for 6 hours in flowing air. A catalyst of the following composition was obtained: $Mo_{12}Bi_{1.0}W_{0.3}Fe_{2.4}Co_{2.0}Ni_{4.0}Sb_{0.7}Cs_{0.6}Mg_{0.5}Zn_{0.5}$.

EXAMPLE 2

The procedure of Example 1 was repeated with the following amounts:

First Solution:
ammonium paramolybdate—45.84 g
ammonium paratungstate—1.72 g

Second Solution:
bismuth nitrate—5.19 g
ferric nitrate—20.78 g
nickel nitrate—24.92 g
cobalt nitrate—12.53 g
magnesium nitrate—2.75 g
zinc nitrate—3.37 g Slurry Addition:
cesium nitrate—2.51 g
antimony oxide—2.20 g The composition of the catalyst was $Mo_{12}Bi_{0.5}W_{0.3}Fe_{2.4}Co_{2.0}Ni_{4.0}Sb_{0.7}Cs_{0.6}Mg_{0.5}Zn_{0.5}$.

EXAMPLE 3

The procedure of Example 1 was repeated except for the following amounts:

First Solution:
ammonium paramolybdate—42.31 g
ammonium paratungstate—1.61 g

Second Solution:
bismuth nitrate—11.63 g
ferric nitrate—23.40 g
nickel nitrate—23.23 g
cobalt nitrate—11.68 g
magnesium nitrate—2.56 g
zinc nitrate—3.14 g Slurry Addition:
cesium nitrate—2.34 g
antimony oxide—2.05 g The composition of the catalyst was $M_{12}Bi_{1.2}W_{0.3}Fe_{2.9}Co_{2.0}Ni_{4.0}Sb_{0.7}Cs_{0.6}Mg_{0.5}Zn_{0.5}$.

EXAMPLE 4

The procedure of Example 1 was repeated except for the following amounts:

First Solution:
ammonium paramolybdate—45.01 g
ammonium paratungstate—0.00 g

Second Solution:
bismuth nitrate—9.99 g
ferric nitrate—19.90 g
nickel nitrate—36.00 g
cobalt nitrate—0.00 g
magnesium nitrate—5.21 g
zinc nitrate—0.00 g Slurry Addition:
cesium nitrate—2.42 g
antimony oxide—2.12 g The ammonium molybdate solution was heated to 95° C. over 45 minutes before the second solution was added and the catalyst precursor was heated to 485° C. with a 10° C./min ramp. The composition of the catalyst was $Mo_{12.3}Bi_{1.0}Fe_{2.4}Ni_{6.0}Sb_{0.7}Cs_{0.6}Mg_{1.0}$.

EXAMPLE 5

The procedure of Example 1 was repeated except for the following amounts:

First Solution:
ammonium paramolybdate—44.63 g
ammonium paratungstate—0.00 g

Second Solution:
bismuth nitrate—10.22 g
ferric nitrate—20.43 g
nickel nitrate—24.51 g
cobalt nitrate—12.33 g
magnesium nitrate—2.70 g
zinc nitrate—3.32 g Slurry Addition:
cesium nitrate—2.47 g
antimony oxide—2.17 g The composition of the catalyst was $M_{12}Bi_{1.0}Fe_{2.4}Co_{2.0}Ni_{4.0}Sb_{0.7}Cs_{0.6}Mg_{0.5}Zn_{0.5}$.

EXAMPLE 6

The procedure of Example 1 was repeated except for the following amounts:

First Solution:
ammonium paramolybdate—44.70 g
ammonium paratungstate—0.00 g

Second Solution:
bismuth nitrate—9.98 g
ferric nitrate—19.94 g
nickel nitrate—23.93 g
cobalt nitrate—12.03 g
magnesium nitrate—2.64 g
zinc nitrate—3.24 g Slurry Addition:
cesiun nitrate—2.41 g
antimony oxide—2.12 g The composition of the catalyst was $Mo_{12.3}Bi_{1.0}Fe_{2.4}Co_{2.0}Ni_{4.0}Sb_{0.7}Cs_{0.6}Mg_{0.5}Zn_{0.5}$.

COMPARATIVE EXAMPLE 1

The procedure of Example 1 was repeated except for the following amounts:

First Solution:
ammonium paramolybdate—46.35 g
ammonium paratungstate—1.76 g

Second Solution:
bismuth nitrate—2.65 g
ferric nitrate—21.21 g
nickel nitrate—25.45 g
cobalt nitrate—12.80 g
magnesium nitrate—2.81 g
zinc nitrate—3.45 g Slurry Addition:
cesium nitrate—2.56 g
antimony oxide—2.25 g The composition of the catalyst was $M_{12}Bi_{0.25}W_{0.3}Fe_{2.4}Co_{2.0}Ni_{4.0}Sb_{0.7}Cs_{0.6}Mg_{0.5}Zn_{0.5}$.

COMPARATIVE EXAMPLE 2

The procedure of Example 1 was repeated except for the following amounts:

First Solution:
ammonium paramolybdate—41.90 g
ammonium paratungstate—1.59 g

Second Solution:
bismuth nitrate—14.39 g
ferric nitrate—19.18 g
nickel nitrate—23.00 g
cobalt nitrate—11.57 g
magnesium nitrate—2.53 g
zinc nitrate—3.12 g Slurry Addition:
cesium nitrate—2.31 g
antimony oxide—2.05 g The composition of the catalyst was $Mo_{12}Bi_{1.5}W_{0.3}Fe_{2.4}Co_{2.0}Ni_{4.0}Sb_{0.7}Cs_{0.6}Mg_{0.5}Zn_{0.5}$.

COMPARATIVE EXAMPLE 3

The procedure of Example 1 was repeated except for the following amounts:

First Solution:
ammonium paramolybdate—42.43 g
ammonium paratungstate—1.61 g

Second Solution:
bismuth nitrate—9.70 g
ferric nitrate—19.38 g
nickel nitrate—11.63 g
cobalt nitrate—23.38 g
magnesium nitrate—2.57 g
zinc nitrate—3.15 g Slurry Addition:
cesium nitrate—4.69 g
antimony oxide—2.05 g The composition of the catalyst was $Mo_{12}Bi_{1.0}W_{0.3}Fe_{2.4}Co_{4.0}Ni_{2.0}Sb_{0.7}Cs_{1.2}Mg_{0.5}Zn_{0.5}$.

COMPARATIVE EXAMPLE 4

The procedure of Example 1 was repeated except for the following amounts:

First Solution:
ammonium paramolybdate—44.33 g
ammonium paratungstate—1.68 g

Second Solution:
bismuth nitrate—8.12 g
ferric nitrate—16.91 g
nickel nitrate—24.34 g
cobalt nitrate—12.24 g
magnesium nitrate—2.68 g
zinc nitrate—3.30 g Slurry Addition:
cesium nitrate—3.27 g
antimony oxide—2.15 g The composition of the catalyst was $Mo_{12}Bi_{0.8}W_{0.3}Fe_{2.0}Co_{2.0}Ni_{4.0}Sb_{0.7}Cs_{0.8}Mg_{0.5}Zn_{0.5}$.

COMPARATIVE EXAMPLE 5

The procedure of Example 1 was repeated except for the following amounts:

First Solution:
ammonium paramolybdate—40.92 g
ammonium paratungstate—1.55 g

Second Solution:
bismuth nitrate—11.24 g
ferric nitrate—22.63 g
nickel nitrate—22.47 g
cobalt nitrate—11.30 g
magnesium nitrate—2.48 g
zinc nitrate—3.04 g Slurry Addition:
cesium nitrate—1.88 g
antimony oxide—4.25 g The composition of the catalyst was $Mo_{12}Bi_{1.2}W_{0.3}Fe_{2.9}Co_{2.0}Ni_{4.0}Sb_{1.5}Cs_{0.5}Mg_{0.5}Zn_{0.5}$.

COMPARATIVE EXAMPLE 6

The procedure of Example 1 was repeated except for the following amounts:

First Solution:
ammonium paramolybdate—45.05 g
ammonium paratungstate—1.71 g

Second Solution:
bismuth nitrate—10.32 g
ferric nitrate—10.31 g
nickel nitrate—24.73 g
cobalt nitrate—12.44 g
magnesium nitrate—2.73 g
zinc nitrate—3.35 g Slurry Addition:
cesium nitrate—2.49 g
antimony oxide—2.18 g The composition of the catalyst was $Mo_{12}Bi_{1.0}W_{0.3}Fe_{1.2}Co_{2.0}Ni_{4.0}Sb_{0.7}Cs_{0.6}Mg_{0.5}Zn_{0.5}$.

COMPARATIVE EXAMPLE 7

The procedure of Example 1 was repeated except for the following amounts:

First Solution:
ammonium paramolybdate—54.46 g
ammonium paratungstate—1.65 g

Second Solution:
bismuth nitrate—9.98 g
ferric nitrate—19.94 g
nickel nitrate—23.92 g
cobalt nitrate—12.03 g
magnesium nitrate—2.64 g
zinc nitrate—3.24 g Slurry Addition:
cesium nitrate—2.41 g
antimony oxide—2.11 g The composition of the catalyst was $Mo_{15}Bi_{1.0}W_{0.3}Fe_{2.4}Co_{2.0}Ni_{4.0}Sb_{0.7}Cs_{0.6}Mg_{0.5}Zn_{0.5}$.

COMPARATIVE EXAMPLE 8

The procedure of Example 1 was repeated except for the following amounts:

First Solution:
ammonium paramolybdate—32.67 g
ammonium paratungstate—1.65 g

Second Solution:
bismuth nitrate—9.98
ferric nitrate—19.94 g
nickel nitrate—23.92 g
cobalt nitrate—12.03 g
magnesium nitrate—2.64 g
zinc nitrate—3.24 g Slurry Addition:
cesium nitrate—2.41 g
antimony oxide—2.11 g The composition of the catalyst was $Mo_{9}Bi_{1.0}W_{0.3}Fe_{2.4}Co_{2.0}Ni_{4.0}Sb_{0.7}Cs_{0.6}Mg_{0.5}Zn_{0.5}$.

COMPARATIVE EXAMPLE 9

The procedure of Example 1 was repeated except for the following amounts:

First Solution:
ammonium paramolybdate—45.52 g
ammonium paratungstate—1.73 g

Second Solution:
bismuth nitrate—6.25 g
ferric nitrate—17.36 g
nickel nitrate—25.00 g
cobalt nitrate—12.57g
magnesium nitrate—2.76 g
zinc nitrate—3.38 g Slurry Addition:
cesium nitrate—2.52 g
antimony oxide—2.21 g The composition of the catalyst was $Mo_{12}Bi_{0.6}W_{0.3}Fe_{2.0}Co_{2.0}Ni_{4.0}Sb_{0.7}Cs_{0.6}Mg_{0.5}Zn_{0.5}$.

COMPARATIVE EXAMPLE 10

The procedure of Example 1 was repeated except for the following amounts:

First Solution:
ammonium paramolybdate—30.35 g
ammonium paratungstate—1.15 g

Second Solution:
bismuth nitrate—4.17 g
ferric nitrate—11.57 g
nickel nitrate—14.78 g
cobalt nitrate—10.26 g
magnesium nitrate—1.84 g
zinc nitrate—2.26 g Slurry Addition:
cesium nitrate—1.68 g
antimony oxide—1.47 g The composition of the catalyst was $Mo_{12}Bi_{0.6}W_{0.3}Fe_{2.0}Co_{2.4}Ni_{3.6}Sb_{0.7}Cs_{0.6}Mg_{0.5}Zn_{0.5}$.

For each of the catalysts from the Examples and Comparative Examples above, 1.0–2.0 cc of catalyst were mixed with quartz chips to make a total volume of 5 cc, which were placed into a downflow reactor having an internal diameter of 0.25 inches. A gas consisting of 3.6% isobutylene, 8.6% oxygen, 28% water and the balance as nitrogen was passed over the catalyst bed in the reactor. The volumetric flow rates were varied between 38 and 85 sccm. The internal reactor temperature and pressure were maintained at 390° C. and 0 psig. The gas hourly space velocity was about 1500 to about 3400 $hr^{-1}$. The catalyst loading and gas flow rate were adjusted such that, where possible, a conversion between 97 and 99% was obtained. Product liquid was condensed into a glass trap maintained at 0° C. for a period of approximately three hours. The yields of methacrylic acid and acetic acid were determined from this liquid. The concentrations of isobutylene, methacrolein and other byproducts were determined from on-line analysis by gas chromatography.

Catalyst activities are reported in Table I relative to example 3, for which 1.5 cc of catalyst at a flow rate of 38 sccm gave 98.0% conversion and 87.4% selectivity to methacrolein. Repeated tests of the catalysts of the Examples suggest that the accuracy of the relative activity number is roughly ±0.05.

It is well known that selectivity for isobutylene oxidation (and indeed most partial oxidation reactions) is dependent on isobutylene conversion; as conversion is increased the selectivity decreases due to further oxidation of the desired products. Given this, the selectivities of two different catalysts must be compared at the same conversion for the comparison to be meaningful. The selectivity of example 1 was measured across a wide range of conversions, from less than 30% to more than 99% and fit a curve to this data over that range. The actual selectivities of examples 2 through 6 and comparative examples 1 through 10 were compared to the selectivity curve that was generated for the catalyst of example 1 at the same conversion. The absolute percent difference between the selectivities of the catalysts of examples 2 through 6 and comparative examples 1 through 10 and the selectivity of example 1 at the same conversion is reported in Table I as "relative selectivity." The measurement error on the relative selectivity number is roughly ±1. Mass balances were measured for every sample and averaged 96%.

ranges of 2–6, 3.3–5 and 0.9 to 1.1, respectively, and have activity higher than that of catalysts of the present invention (Comparative Examples 1, 5 and 7 at 1.97, 1.27 and 1.42 relative activity) have selectivities which are unsuitable for good catalyst performance (−2, −5 and −3 relative selectivity).

EXAMPLE 7

The procedure of Example 1 was repeated.

The composition of the catalyst was $Mo_{12}Bi_{1.0}W_{0.3}Fe_{2.4}Co_{2.0}Ni_{4.0}Sb_{0.7}Cs_{0.6}Mg_{0.5}Zn_{0.5}$.

COMPARATIVE EXAMPLE 11

The procedure of Example 1 was repeated except for the following amounts:

First Solution:

ammonium paramolybdate—42.94 g
ammonium paratungstate—1.63 g

Second Solution:

bismuth nitrate—9.83 g
ferric nitrate—19.65 g
nickel nitrate—23.58 g
cobalt nitrate—11.85 g

TABLE I

| | | | $Mo_{12}Bi_aW_bFe_cCo_dNi_eSb_fCs_gMg_hZn_iP_jO_x$ | | |
|---|---|---|---|---|---|
| EXAMPLE | c/a | c/g | (3a + 3c + 2d + 2e + g + 2h + 2i)/(2 × 12 + 2b) | RELATIVE ACTIVITY | RELATIVE SELECTIVITY |
| 1 | 2.4 | 4.0 | 1.01 | 1.09 | Same |
| 2 | 4.8 | 4.0 | 0.95 | 1.44 | Same |
| 3 | 2.4 | 4.8 | 1.09 | 1.00 | — |
| 4 | 2.4 | 4.0 | 1.06 | 1.01 | Same |
| 5 | 2.4 | 4.0 | 1.03 | 1.01 | Same |
| 6 | 2.4 | 4.0 | 1.0 | 1.34 | +1 |
| COMPARATIVE 1 | 9.6 | 4.0 | 0.92 | 1.97 | −2 |
| COMPARATIVE 2 | 1.7 | 4.0 | 1.07 | 0.57 | Same |
| COMPARATIVE 3 | 2.4 | 2.0 | 1.03 | 0.39 | Same |
| COMPARATIVE 4 | 2.5 | 2.5 | 0.94 | 0.84 | −2 |
| COMPARATIVE 5 | 2.4 | 5.8 | 1.09 | 1.27 | −5 |
| COMPARATIVE 6 | 1.2 | 2.0 | 0.86 | 0.80 | −2 |
| COMPARATIVE 7 | 2.4 | 4.0 | 0.81 | 1.42 | −3 |
| COMPARATIVE 8 | 2.4 | 4.0 | 1.33 | 0.12 | −3 |
| COMPARATIVE 9 | 3.3 | 3.3 | 0.91 | 0.90 | Same |
| COMPARATIVE 10 | 3.3 | 3.3 | 0.91 | 0.96 | Same |

The above examples demonstrate the effectiveness of the relative amount ratios of certain components to certain other components in a mixed metal oxide catalyst for the catalytic oxidation of an olefin to an unsaturated aldehyde, e.g., propylene or isobutylene to acrolein or methacrolein. Those catalysts which have ratios of iron to bismuth, iron to cesium and bismuth, iron, cobalt, nickel, cesium, magnesium and zinc to molybdenum and tungsten which are within the ranges of 2.4–4.8, 4.0–4.8, and 0.95–1.09, respectively, have activity better than and selectivity as good or better than those catalysts having any one of these ratios outside the ranges of 2–6, 3.3–5 and 0.95 to 1.1, respectively. The catalysts which have a ratio outside the ranges of 2–6, 3.3–5 and 0.95 to 1.1, respectively, and have selectivity as good as that of catalysts of the present invention (Comparative Examples 2, 3, 9 and 10) have activity which is unsuitable for good catalyst performance (0.57, 0.39, 0.90, 0.96 relative activity). Those catalysts which have ratios outside the magnesium nitrate—2.60 g
zinc nitrate—3.19 g Slurry Addition:

thallium nitrate—3.24 g
antimony oxide—2.08 g

The composition of the catalyst was $M_{12}Bi_{1.0}W_{0.3}Fe_{2.4}Co_{2.0}Ni_{4.0}Sb_{0.7}Tl_{0.6}Mg_{0.5}Zn_{0.5}$.

For each of the catalysts from the Examples and Comparative Examples above, 1.5 cc of catalyst were mixed with quartz chips to make a total volume of 5 cc, which were placed into a downflow reactor having an internal diameter of 0.25 inches. A gas consisting of 3.6% isobutylene, 8.6% oxygen, 28% water and the balance as nitrogen was passed over the catalyst bed in the reactor. The volumetric flow rates were about 250 sccm. The internal reactor temperature and pressure were maintained at 380° C. and 55 psig. The gas hourly space velocity was about 10,000 $hr^{-1}$. The concentrations of isobutylene, methacrolein and other byproducts were determined from on-line analysis by gas chromatography.

Catalyst activities are reported in Table II relative to example 7, for which 1.5 cc of catalyst at a flow rate of 250 sccm gave 80.0% conversion and 87.4% selectivity to methacrolein. Example 7 is defined to have relative activity of 1.0 and relative selectivity of zero.

TABLE II

| EXAMPLE | Cs | Tl | RELATIVE ACTIVITY | RELATIVE SELECTIVITY |
|---|---|---|---|---|
| 7 | 0.6 | 0.0 | 1.0 | — |
| COMPARATIVE 11 | 0.0 | 0.6 | 2.8 | −12 |

The above examples demonstrate the effectiveness of the presence of cesium relative to certain other components. i.e., thallium, in a mixed metal oxide catalyst for the catalytic oxidation of an olefin to an unsaturated aldehyde, e.g., propylene or isobutylene to acrolein or methacrolein. While the activity of the catalyst containing thallium is higher than that of the catalyst containing cesium, the selectivity is significantly lower.

EXAMPLE 8

The catalyst of Example 3 ($Mo_{12}Bi_{1.2}W_{0.3}Fe_{2.9}Co_{2.0}Ni_{4.0}Sb_{0.7}Cs_{0.6}Mg_{0.5}Zn_{0.5}$) was tested per the conditions below.

COMPARATIVE EXAMPLE 12

The catalyst of Comparative Example 10 ($Mo_{12}Bi_{0.6}W_{0.3}Fe_{2.0}Co_{2.4}Ni_{3.6}Sb_{0.7}Cs_{0.6}Mg_{0.5}Zn_{0.5}$) was tested per the conditions below.

For each of the catalysts from Example 8 and Comparative Example 12 above, 1.5 cc of catalyst were mixed with quartz chips to make a total volume of 5 cc, which were placed into a downflow reactor having an internal diameter of 0.25 inches. A gas consisting of 3.6% isobutylene, 8.6% oxygen, 28% water and the balance as nitrogen was passed over the catalyst bed in the reactor. The volumetric flow rates were about 250 sccm. The internal reactor temperature and pressure were maintained at 370° C. and 55 psig. The gas hourly space velocity was about 10,000 $hr^{-1}$. The concentrations of isobutylene, methacrolein and other byproducts were determined from on-line analysis by gas chromatography.

Catalyst activities are reported in Table III relative to Example 8, for which 1.5 cc of catalyst at a flow rate of 250 sccm gave 94.8% conversion and 81% selectivity to methacrolein.

TABLE III

| EXAMPLE | RELATIVE ACTIVITY | RELATIVE SELECTIVITY |
|---|---|---|
| 8 | 1.00 | — |
| COMPARATIVE 12 | 0.96 | −2 |

Better selectivity was obtained with the catalyst of Example 8 than for the catalyst of Comparative Example 12 at a gas hourly space velocity of about 10,000 $hr^{-1}$ and a pressure of 55 psig while the same catalysts (Example 3 and Comparative Example 10) have approximately the same selectivity at a gas hourly space velocity of about 1500 to about 3400 $hr^{-1}$ and a pressure of 0 psig. Commercial operation will require higher gas hourly space velocities of 7500 to 12,500 $hr^{-1}$ due to the pressure drop across the reactor and the pressure head needed to push reactants and products downstream. Therefore, the catalysts of the present invention will perform better under commercial conditions than catalysts not having the claimed relative amount ratios of cesium to bismuth, of iron to bismuth and of bismuth, iron, cesium and certain other metals to molybdenum and, optionally, tungsten.

Obviously, numerous modifications and variations of the present invention are possible in light of the above teachings. It is therefore to be understood that within the scope of the appended claims, the invention may be practiced otherwise than as specifically described herein.

What is claimed is:

1. A catalyst for the oxidation of an olefin to an unsaturated aldehyde comprising a mixed metal oxide having the formula:

$$Mo_{12}Bi_aW_bFe_cCs_gM_mO_x$$

wherein a is in the range from 0.1 to 1.5, b is in the range from 0 to 9, c is in the range from 0.2 to 5.0, g is in the range from 0.1 to 1.5, M is one or more selected from the group consisting of calcium, strontium, lithium, sodium, selenium, cobalt, nickel, magnesium, zinc, potassium, rubidium, thallium, manganese, barium, chromium, tin, lead, cadmium and copper, m is in the range from 0 to 9, x is determined by the valences of the other components and wherein the relative amount ratio of c to g is from 3.3 to 5.0, the relative amount ratio of c to a is from 2.0 to 6.0 and the relative amount ratio of $(3a+3c+g+\Sigma v_n m_n)/(2\times12+2b)$ is from 0.95 to 1.10 with v being valence of each M, and n being the total number of M.

2. The catalyst of claim 1 wherein g is in the range from 0.4 to 1.5.

3. The catalyst of claim 1 wherein the mixed metal oxide is having the formula:

$$M_{12}Bi_aW_bFe_cCs_gM_mM'_{m'}O_x$$

wherein M' is one or more selected from the group consisting of cerium, antimony, phosphorus, boron, sulfur, silicon, aluminum, titanium, tellurium, vanadium, zirconium and niobium, m' is in the range from 0 to 9.

4. The catalyst of claim 3 wherein the mixed metal oxide is of the formula:

$$Mo_{12}Bi_aW_bFe_cCo_dNi_eSb_fCs_gMg_hZn_iP_jO_x$$

wherein b is 0 to 4, d is 0 to 9, e is 0 to 9, f is 0 to 2.0, h is 0 to 1.5, i is 0to 2.0, j is 0 to 0.5 and wherein the relative amount ratio of (3a+3c+2d+2e+g+2h+2i)/(2×12+2b) is from 0.95 to 1.10.

5. The catalyst of claim 4 wherein the relative amount ratio of c to a is from 2.4 to 4.8, the relative amount ratio of c to g is from 4.0 to 4.8 and the relative amount ratio of (3a+3c+2d+2e+g+2h+2i)/(2×12+2b) is from 0.95 to 1.09.

6. The catalyst of claim 5 wherein the catalyst has an X-ray diffraction pattern of diffraction peaks at the diffraction angles of 2θ, measured by using Cu Kα radiation, at 25.5, 26.6 and 28.0.

7. The catalyst of claim 5 wherein the catalyst is unsupported and has a surface area of from 0.1 to 150 $m^2/g$.

8. The catalyst of claim 7 wherein the catalyst has a surface area of from 1 to 20 $m^2/g$.

9. The catalyst of claim 1 wherein the mixed metal oxide is supported on an inert support.

10. The catalyst of claim 9 wherein the inert support is silica, alumina, niobia, titania, zirconia or mixtures thereof.

11. The catalyst of claim 1 wherein the catalyst is in the form of powder, granules, spheres, cylinders or saddles.

* * * * *